(12) United States Patent
Mizuguchi et al.

(10) Patent No.: US 6,921,663 B2
(45) Date of Patent: Jul. 26, 2005

(54) ADENOVIRUS VECTOR

(75) Inventors: Hiroyuki Mizuguchi, Tokyo (JP); Takao Hayakawa, Tokyo (JP)

(73) Assignee: National Institute of Health Sciences, Tokyo (JP)

( * ) Notice: Subject to any disclaimer, the term of this patent is extended or adjusted under 35 U.S.C. 154(b) by 0 days.

(21) Appl. No.: 09/845,160

(22) Filed: May 1, 2001

(65) Prior Publication Data

US 2002/0058045 A1 May 16, 2002

(30) Foreign Application Priority Data

May 31, 2000 (JP) ........................................ 2000-161577
Apr. 27, 2001 (JP) ........................................ 2001-131688

(51) Int. Cl.$^7$ ........................ C12N 15/86; C12N 15/861
(52) U.S. Cl. ................. 435/320.1; 424/93.1; 424/93.2; 424/185.1; 424/186.1; 424/199.1; 424/233.1; 435/69.1; 435/455; 435/456; 536/23.72; 935/23; 935/56
(58) Field of Search ............................. 424/93.1, 93.2, 424/159.1, 185.1, 186.1, 149.1, 192.1, 196.1, 233.1; 435/7.1, 91.4, 295.1, 320.1, 456, 173.3, 455, 458, 69.1; 514/44; 530/350; 536/23.1, 23.72; 935/23, 56

(56) References Cited

U.S. PATENT DOCUMENTS 6,210,946 B1  4/2001  Curiel et al. ................ 424/93.2

FOREIGN PATENT DOCUMENTS

WO  WO 99/39734  8/1999
WO  WO 00/12738  3/2000

OTHER PUBLICATIONS

Merchlinsky et al. Introduction of foreign DNA into the vaccinia virus genome by in vitro ligation: recombination–independent selectable cloning vectors. Virology (1992) vol. 190, pp. 522–526.*

Rixon et al. Insertion of DNA sequences at a unique restriction enzyme site engineered for vector purposes into the genome of herpes simplex virus type 1. Journal of General Virology (1990) vol. 70, pp. 2931–2939.*

Dmitriev et al. An adenovirus vector with genetically modified fibers demonstrates expanded tropism.via ultilization of a coxsackievirus and adenovirus receptor–independent cell entry mechanisms. Journal of Virology (1998) vol. 72, No. 12, pp. 9706–9713.

Krasnykh et al. Characterization of an adenoviral vector containing a heterologous peptide epitope in the HI loop of the fiber knob. Journal of Virology (1998), vol. 72, No. 3, pp. 1844–1852.

Arap et al. Cancer treatment by targeted drug delivery to tumor vasculature in a mouse model. Science (1998) vol. 279, pp. 377–380.

Liqiong LIU et al., "Incorporation of Tumor Vasculature Targeting Motifs into Moloney Murine Leukemia Virus Env Escort Proteins Enhances Retrovirus Binding and Transduction of Human Endothelial Cells", Journal of Virology, vol. 74, No. 11, Jun. 2000, pp. 5320–5328.

* cited by examiner

Primary Examiner—Ulrike Winkler
(74) Attorney, Agent, or Firm—Foley & Lardner LLP (57) ABSTRACT

The present invention provides a method for constructing a fiber-mutant adenovirus vector in which a foreign peptide is introduced by a simple system into the fiber HI loop-coding gene of adenovirus; and provides a fiber-mutant adenovirus vector which is constructed by this method.

9 Claims, 6 Drawing Sheets

SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Peptide
      having affinity with heparan sulfate.

<400> SEQUENCE: 1

Lys Lys Lys Lys Lys Lys Lys
1               5

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Peptide
      having affinity with laminin receptor.

<400> SEQUENCE: 2

Thr Ser Gly Tyr Ile Gly Ser Arg Gly Tyr Ile Gly Ser Arg Gly Tyr
1               5                   10                  15

Ile Gly Ser Arg Ser Ser
            20

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Peptide
      having affinity with laminin receptor.

<400> SEQUENCE: 3

Thr Ser Ala Ala Ser Ile Lys Val Ala Val Ser Ile Lys Val Ala Val
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Peptide
      having affinity with E-selectin.

<400> SEQUENCE: 4

Thr Arg Ser Asp Ile Thr Trp Asp Gln Leu Trp Asp Leu Met Lys Thr
1               5                   10                  15

Ser

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: RGD-4C
      peptide.

<400> SEQUENCE: 5

Cys Asp Cys Arg Gly Asp Cys Phe Cys
1               5

-continued

```
<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: NGR
      associating peptide.

<400> SEQUENCE: 6

Cys Asn Gly Arg Cys Val Ser Gly Cys Ala Gly Arg Cys
 1               5                  10

<210> SEQ ID NO 7
<211> LENGTH: 81
<212> TYPE: DNA
<213> ORGANISM: Artificial Sequence
<220> FEATURE:
<223> OTHER INFORMATION: Description of Artificial Sequence:
      Oligonucleotide 1.

<400> SEQUENCE: 7
aacaggagac acaacttcga acatcgatcc aagtgcatac tctatgtcat tttcatggga    60
ctggtctggc cacaactaca t                                             81

<210> SEQ ID NO 8
<211> LENGTH: 79
<212> TYPE: DNA
<213> ORGANISM: Artificial Sequence
<220> FEATURE:
<223> OTHER INFORMATION: Description of Artificial Sequence:
      Oligonucleotide 2.

<400> SEQUENCE: 8
taatgtagtt gtggccagac cagtcccatg aaaatgacat agagtatgca cttggatcga    60
tgttcgaagt tgtgtctcc                                                79

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide 3.

<400> SEQUENCE: 9
cgttaattaa                                                          10

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide 4.
<221> NAME/KEY: CDS
<222> LOCATION: (3)..(29)

<400> SEQUENCE: 10 cg aag tgt gac tgc cgc gga gac tgt ttc tg                           31
   Lys Cys Asp Cys Arg Gly Asp Cys Phe Cys
    1               5                  10

<210> SEQ ID NO 11
<211> LENGTH: 31
<212> TYPE: DNA
<213> ORGANISM: Artificial Sequence
```

```
-continued

<220> FEATURE:
<223> OTHER INFORMATION: Description of Artificial Sequence:
      Oligonucleotide 5.

<400> SEQUENCE: 11
cgcagaaaca gtctccgcgg cagtcacact t                              31

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide 6.

<400> SEQUENCE: 12
cggctgcaac ggccgctgcg tgagcggctg cgccggccgc tg                  42

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide 7.

<400> SEQUENCE: 13
cgcagcggcc ggcgcagccg ctcacgcagc ggccgttgca gc                  42

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 14

Lys Cys Asp Cys Arg Gly Asp Cys Phe Cys
 1               5                  10
```

ADENOVIRUS VECTOR

FIELD OF THE INVENTION

The present invention relates to a method for constructing a fiber-mutant adenovirus vector which comprises introducing a foreign peptide into the HI loop of the fiber of the virus.

BACKGROUND OF THE INVENTION

Adenovirus vectors have been extensively used as attractive vehicles to deliver foreign genes to a variety of cell types in vitro and in vivo.

Adenovirus lacks an envelope and is icosahedral in shape consisting of 252 capsomeres. Twelve capsomeres at each corner are called pentons (consisting of a penton base and fiber) having a protruding structure and the other 240 capsomeres are called hexons. Adenovirus penetrates into a cell (infection) by binding its fiber to a receptor CAR (for detail, see Bergelson J. M. et al., Isolation of a common receptor for Coxsackie B viruses and adenoviruses 2 and 5. Science 275:1320–1323, 1997), and by binding RGD motif of the penton base to integrin on the cell surface (Bai M, Harfe B, Freimuth P, Mutations that alter an Arg-Gly-Asp (RGD) sequence in the adenovirus type 2 penton base protein abolish its cell-rounding activity and delay virus reproduction in flat cells., J Virol 67: 5198–5205, 1993; Wickham T J et al., Integrins αvβ3 and αvβ5 promote adenovirus internalization but not virus attachment. Cell 73: 309–319, 1993). When the virus reaches the endosome, the virus changes its conformation of the capsid protein under acidic conditions, thereby disrupting the endosome and penetrating into the cytoplasm. Since the first step is binding of the viral fiber to CAR which is a receptor on the cell surface, modifying the fiber may change the infection area of adenovirus vector (Paillard, F., Dressing up adenoviruses to modify their tropism. Hum Gene Ther 10:2575–2576, 1999).

A fiber gene is located in the L5 region of an adenovirus late gene. The fiber gene of adenovirus Type 5 consists of 581 amino acids and forms a trimer. The structure is composed of a tail, shaft, and knob part. A knob at the C-terminus binds to a receptor, CAR.

One of difficulties in the use of conventional adenovirus vectors is that the infection areas of the vectors have no tissue-specificity, and therefore the vectors transfer to many tissue cells non-specifically when they are administered systemically. Another difficulty is that the vectors cannot infect cells, which do not express adenovirus receptors (coxackievirus-adenovirus receptor (CAR); e.g., receptors for adenovirus Type 2 and 5 generally used as vectors for gene therapy. See Bergelson J. M. et al., supra for detail.).

Originally, adenovirus vectors, which have poly-lysine sequences having affinity for heparan sulfate at the C-terminus of the fiber molecule, have been constructed. These vectors have been reported to have wide infection area as expected (Wickham T J et al., Increased in vitro and in vivo gene transfer by adenovirus vectors containing chimeric fiber proteins., J. Virol. 71:8221–8229, 1997; Yoshida Y et al., Generation of fiber-mutant recombinant adenoviruses for gene therapy of malignant glioma., Hum Gene Ther 9:2503–2515, 1998; Gonzalez R et al., Increased gene transfer in acute myeloid leukemic cells by an adenovirus vector containing a modified fiber protein., Gene Ther. 6: 314–320, 1999; Bouri K et al., Poly-lysine Modification of adenoviral fiber protein enhances muscle cell transduction., Hum Gene Ther 10: 1633–1640, 1999).

However, it has been shown that insertion of a foreign peptide into the C-terminus of the fiber inhibits the fiber from forming a trimer; the vector has a viral titer 1 to 2 orders of magnitude less than that of a vector having wild type fibers; and the C-termrinus of the fiber is oriented towards the inside of the virus. Therefore, it is now thought that the region is not an optimal site for insertion of a foreign peptide.

In 1998, the group of Curiel et al. have directed their attention to the structure of the HI loop protruding from the viral surface, and have reported that insertion of a foreign peptide into the HI loop of the fiber enables exposure of the peptide on the viral surface, and this does not inhibit viral proliferation at all (Krasnykh V I et al., Characterization of an adenovirus vector containing a heterologous peptide epitope in the HI loop of the fiber knob., J Virol 72: 1844–1852, 1998; Dmitriev I et al., An adenovirus vector with genetically modified fibers demonstrates expanded tropism via utilization of a Coxsackievirus and adenovirus receptor-independent cell entry mechanism., J Virol 72: 9706–9713, 1998). This report indicates a possibility that the HI loop of the fiber is an optimal expression site of a foreign peptide. However, they have constructed such a vector by the method using homologous recombination with special E.coli strain. Thus, the method is not simple enough to be widely used.

SUMMARY OF THE INVENTION

The purpose of the invention is to provide a method for constructing a fiber-mutant adenovirus vector which comprises introducing with a simple system an optional peptide into a fiber HI loop-coding gene sequence.

The inventors of the invention have studied extensively and intensively to solve the above problems, and have completed the present invention by finding that insertion of a unique restriction enzyme recognition site into a gene region encoding the HI loop of the fiber enables simple introduction of oligo DNA encoding an optional peptide into the region.

Accordingly, the present invention relates a method for constructing a fiber-mutant adenovirus vector which comprises inserting a unique restriction enzyme recognition sequence into a fiber HI loop-coding gene sequence, and introducing a foreign peptide-coding DNA into the gene sequence.

Furthermore, the present invention is a fiber-mutant adenovirus vector which is constructed by the above method.

Furthermore, the present invention is an adenovirus vector which contains a unique restriction enzyme recognition site in the fiber HI loop-coding gene sequence.

This specification includes part or all of the contents as disclosed in the specifications and/or drawings of Japanese Patent Application Nos. 2000-161577 and 2001-131688, which are priority documents of the present application.

BRIEF DESCRIPTION OF THE DRAWINGS

An oligonucleotide shown for pAdHM15, is designed so that a positive clone having the oligonucleotide inserted therein is digested with Csp45I but is not digested with ClaI.

Lane 1: 1kb DNA ladder marker

Lane 2: pAdHM15-RGD digested with HindIII/PacI.

Lane 3: pAdHM15-RGD digested with Csp45I/PacI

Lane 4: pAdHM15-RGD-LacZ digested with HindIII/PacI

Lane 5: pAdHM15-RGD-LacZ digested with Csp45I/PacI

Lane 6: AdHM15-RGD-LacZ virus DNA digested with HindIII

Lane 7: AdHM15-RGD-LacZ virus DNA digested with Csp45I.

(B) HindIII and Csp45I restriction map for recombinant adenovirus vector (AdHM15-RGD-LacZ). Fragment size (kb) is shown top or bottom of the genome. CMV denotes a intermediate-early promoter/enhancer of cytomegalovirus, and P(A) denotes a bovine growth hormone polyadenylation signal.

DETAILED DESCRIPTION OF THE INVENTION

A more detailed description of the present invention will be provided as follows.

A method for constructing a fiber-mutant adenovirus vector according to the invention comprises inserting a unique restriction enzyme recognition sequence into a fiber HI loop-coding gene sequence, thereby introducing a foreign peptide-coding DNA into the gene sequence.

The term "fiber HI loop-coding gene sequence" indicates a nucleolide sequence encoding a region from amino acid 537 to 549 of a fiber molecule. Most of the amino acids of the HI loop have a hydrophilic group and are oriented towards the outside of the knob domains. Insertion of a foreign peptide into this region does not affect the formation of trimers by the fiber molecules. For example, this region corresponds to a region from positions 32647 to 32685 of the adenovirus type 5 genomic DNA.

The term "unique restriction enzyme recognition sequence" indicates a restriction enzyme recognition sequence which is not originally present in adenovirus genomic DNA. Examples of such a sequence include sequences recognized by restriction enzymes Csp45I, ClaI, SwaI, PacI, I-CeuI, PI-SceI, I-PpoI, and I-SceI.

When Csp45I and ClaI are used as unique restriction enzymes, these enzymes produce adhesive ends compatible for each other so that the oligonucleotide above can be inserted in any direction. That is, the above oligonucleotide is so designed that a positive clone, in which an oligonucleotide is inserted forwardly, contains Csp45I recognition sequence, but does not contain ClaI recognition sequence. This enables facilitated identification of the positive clone based on the difference in cleavage patterns between restriction enzymes Csp45I and ClaI. An example of the thus designed oligonuleotide is not limited and is an oligonucleotide comprising nucleotide sequences of SEQ ID NOS: 10 to 13.

For example, the above-mentioned recognition sequence can be inserted into a HI loop-coding gene sequence according to the Example of the invention.

DNA encoding a foreign peptide can be introduced, for example by synthesizing oligonucleotide DNA having the peptide-coding DNA and the unique restriction enzyme recognition sequence above, and by ligating the synthesized oligonucleotide DNA directly into the HI loop-coding sequence digested with the corresponding enzymes.

Examples of DNA encoding a foreign peptide include, but are not limited to, DNA encoding a peptide containing RGD, DNA encoding a peptide containing NGR, DNA encoding a peptide (KKKKKKK: SEQ ID NO: 1) having affinity for heparan sulfate, DNA encoding a peptide (TS(GYIGSR) $_3$SS: SEQ ID NO: 2 or TSAA(SIKVAV)$_2$: SEQ ID NO: 3) having affinity for a laminin receptor, DNA encoding a peptide (TRSDITWDQLWDLMKTS: SEQ ID NO: 4) having affinity for E-selectin. Selection of the DNAs above can improve the efficiency of gene introduction into destinations (e.g., tissues and cells) of vectors. In other word, by selecting peptides which have been reported to have tropism for tumor vascular endothelial cells as foreign peptide, such as those containing RGD and NGR, vectors useful in treating various tumors can be constructed.

Peptides containing RGD are not limited as long as they have RGD sequence and have binding affinity to integrins on the cell surface. Such a peptide preferably consists of 5 to 20 amino acids including RGD, and more specifically, a RGD-4C peptide (CDCRGDCFC: SEQ ID NO: 5).

Since an adenovirus vector with the RGD-4C peptide has binding affinity to integrins in addition to CAR, selection of this peptide as a foreign peptide can improve the efficiency of gene introduction not only to adenovirus-sensitive cells, but also to cells, to which conventional virus vectors cannot be applied due to poor expression of CAR, such as CHO cells, respiratory epidermic cells, smooth muscle cells, vascular endothelial cells, T-cells, macrophages, hepatopoietic stem cells, dendritic cells, and cancer cells which are CAR-negative but expressing integrins on their surfaces (e.g., human glioma cell LN444).

Examples of peptides containing NGR are not limited as long as they contain NGR sequence and have binding affinity for amino peptidase N (CD13) on the cells surface. Such a peptide preferably comprises 5 to 20 amino acids including NGR. Specifically, such a peptide is NGR-associated peptide (CNGRCVSGCAGRC: SEQ ID NO: 6).

Since an adenovirus vector with the NGR-associated peptide has binding affinity to aminopeptidase N/CD13 in addition to CAR, selection of this peptide as a foreign peptide can achieve specific gene integration not only to adenovirus-sensitive cells, but also to cells, to which conventional virus vectors cannot be applied due to poor expression of CAR, such as CD13 expression cells (e.g., human glioma cell LN444) of for example, cancer neovessel.

PREFERRED EMBODIMENTS FOR CARRYING OUT THE INVENTION

The present invention is further described in the following examples. The examples are provided for illustrative purposes only, and are not intended to limit the scope of the invention.

EXAMPLE 1

Preparation of Adenovirus Vector Having a Foreign Peptide Added to the HI Loop of the Fiber-1

Throughout the present Examples, the recognition sites of unique restriction enzymes, Csp45I and ClaI, were applied to a gene sequence portion encoding the HI loop of the fiber.

First, vector plasmids, pAdHM 15, 16, 17 and 18 were constructed as follows.

A plasmid pEco-ITR1 comprising the right terminal portion of adenovirus type 5 genome (which corresponds to a portion from the base at position 27,331 to the right terminus with the E3 region deleted (positions 27,865 to 30,995)) was cleaved with restriction enzymes ApaI and MunI, and ligated with the ApaI/MunI fragment of pBR-AM2, which is a pBR322-derived plasmid with an AgeI and a MunI site between the AatII and BsaI sites and a deletion between the PvuII and Bst1107I sites. The resulting plasmid, pBR-AM3, contained positions 31,905 to 32,825 of adenovirus genome.

Then, a 4-pieces ligation reaction was carried out to obtain a plasmid pBR-AM4, using each of ApaI/AseI restriction fragments, ApaI/BsmAI restriction fragments and BsaAI restriction fragments of pBR-AM3, and oligonucleotide 1 (5'-AACAGGAGACACAAC TTCGAAC[ATCGAT]CCAAGTGCATACTCTATGT CATTTTCATGGGACTGGTCTGGCCACAACTACAT-3', SEQ ID NO: 7) and oligonucleotide 2 (5'-TAATGTAGTTGTGGCCAGACCAGTC-CCATGAAAATGACATAGAGTATGCACTTGG[ATCGAG]GTTCGAAGTTGTGTCTCC-3', SEQ ID NO: 8) (underlines and parentheses herein denote the recognition sites of Csp45I and ClaI, respectively, which were methylated with diantipyrylmethane (Dam)).

After that, HpaI/MunI restriction fragments of pBR-AM4 were ligated with the HpaI/MunI restriction fragments of pEco-ITR5 (which comprises the right terminus of adnovirus type 5 genome, corresponding to a portion from the base at position 27,331 to the right terminus of the genome with the E3 region deleted (positions 28,133 to 30,818)), thereby constructing pEco-AM4.

Figure 1A:
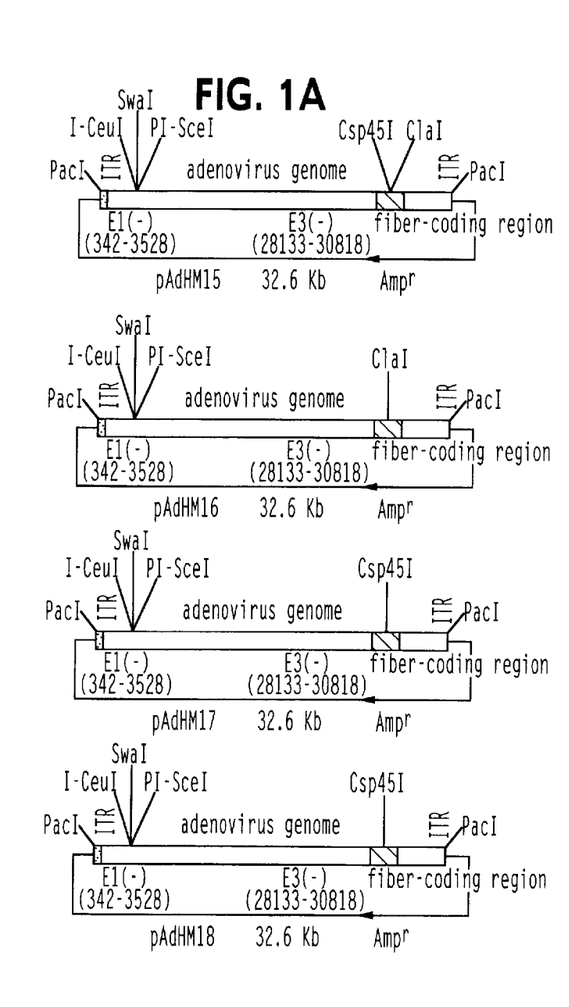
FIG. 1 shows the characteristics of the vector plasmids of the invention. (A) Vector plasmid pAdHM15, 16, 17 and 18 contain E1/E3-deleted adenovirus genomic DNA,: Csp45I and/or ClaI site between positions 32679 and 32680 of the adenoviral genomic DNA, and I-CeuI/SwaI/PI-SceI sites in the E1-deletion region. (B) Sequences around a foreign oligonucleotide insertion site are shown for each vector plasmid. Foreign oligonucleotides are indicated in italics. (C) Oligonucleotides synthesized for each plasmid vector.

Finally, the SrfI/ClaI restriction fragments of AdHM2-1, which is a pAdHM2 derivative, were ligated with the SrfI/ClaI restriction fragments of the above pEco-AM4, and then the ligation of the ClaI recognition sequence of the right terminus of adenovirus genome was performed, using oligonucleotide 3 (5'-TTAATTAA-3', SEQ ID NO: 9; herein, an underline denotes a PacI recognition sequence), so that pAdHM15 was obtained, substituting with PacI recognition sequence. Each of pAdHM 16, 17 and 18 was constructed by the same process as for pAdHM15 (FIG. 1A).

Figure 1B:
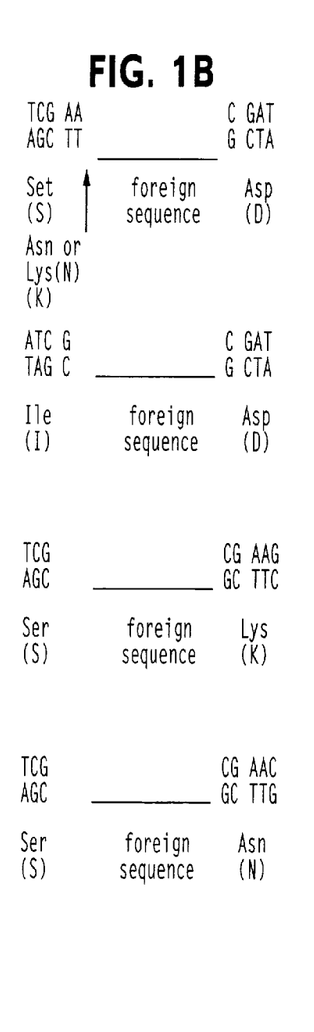
Figure 1C:
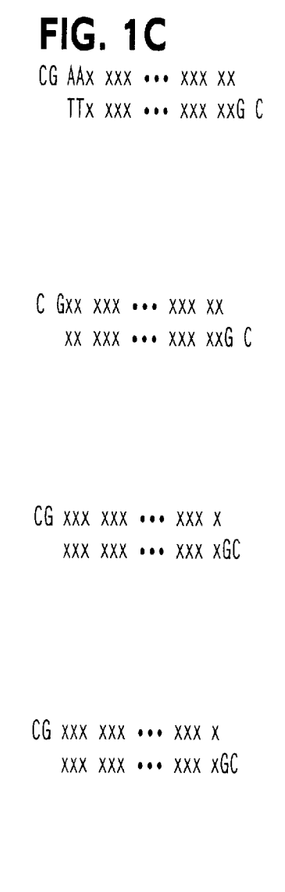

The plasmids pAdHM 15, 16, 17 and 18 had total adenovirus genomes except E1 and E3 regions; these plasmids had I-CeuI, SwaI and PI-SceI recognition sequences of a unique site in the E1-deleted regions, and further, pAdHM15 had Csp45I and ClaI recognition sequences (which were methylated with Dam), pAdHM16 had ClaI recognition sequence, and pAdHM 17 and 18 had Csp45I recognition sequences, between the positions 32,679 and 32,680 of the genome (which correspond to threonine residue (position 546) and proline residue (position 547) of fiber protein, respectively) (FIG. 1). The HI loop region of each plasmid had a newly added 2 or 3 amino acids different from one another, depending on its restriction enzyme recognition sequence, resulting in various applications depending on purpose.

Next, a plasmid vector having oligonucleotide DNAs corresponding to a foreign peptide were constructed.

As a foreign peptide, RGD-4C peptide (CDCRGDCFC, SEQ ID NO: 5) was selected, and oligonucleotide DNAs (oligonucleotides 4 and 5) corresponding to this peptide were used.

First, pAdHM15 constructed as above was cleaved with Csp45I/ClaI, and then ligated with oligonucleotide 4 (5'-CGAAGTGTGACTGCCGCGGAGACTGTTTCTG-3', SEQ ID NO: 10) and oligonucleotide 5 (5'-CGCAGAAACAGTCTCC GCGGCAGTCACACTT-3', SEQ ID NO: 11).

Figure 2:
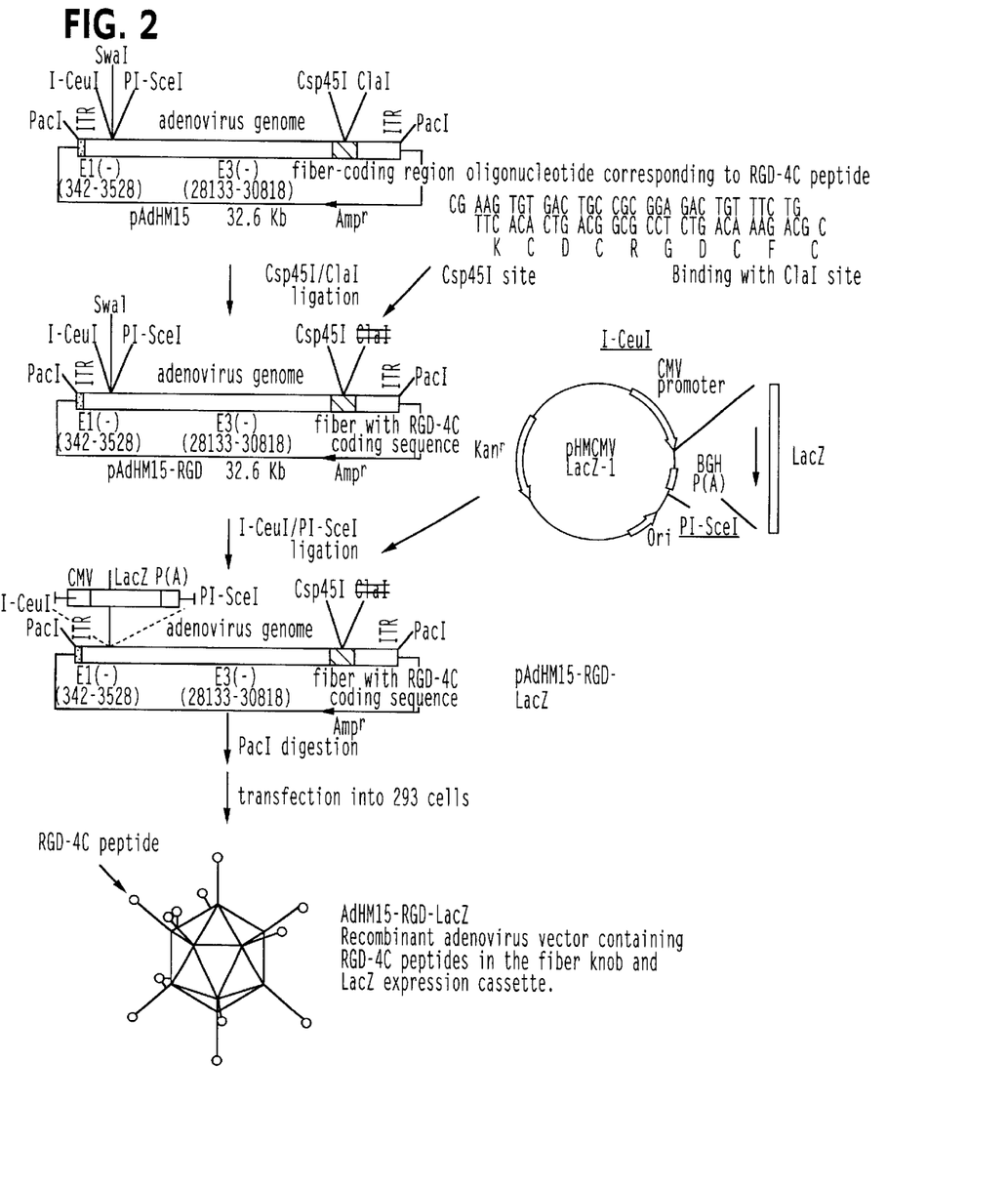
FIG. 2 (SEQ ID NOS 10, 11 & 14) shows a strategy for construction of an adenovirus vector containing RGD-4C peptide in the HI loop of the fiber knob, and containing LacZ expression cassette in E1-deletion region.

Then, the above-ligated DNA was introduced into an *Escherichia coli* DH5 strain to transform the strain, thereby obtaining pAdHM15-RGD (FIG. 2). In respect: of pAdHM 15, 16, 17 and 18, the sequences in the vicinity of each foreign oligonucleotide insertion site, and the possible oligonucleotides syntehsized to each of the above vector plasmids, are shown in FIG. 1. (referred as B and C, respectively).

Cleavage by restriction enzymes Csp45I and ClaI provides cohesive termini having compatibility with each other, which are able to insert the above oligonucleotides in any direction. So, these oligonucleotides were designed in such a manner that a positive plasmid (wherein an oligonucleotide was inserted in a forward direction) comprised a Csp45I recognition sequence but did not comprise a ClaI recognition sequence (FIG. 2.) Both self-ligated plasmids and plasmids wherein the above oligonucleotide was inserted in reverse direction did not comprise a Csp45I recognition sequence. Accordingly, a positive clone could easily be identified by the difference of cleavage pattern of restriction enzymes Csp45I and ClaI. Furthermore, it was confirmed by gene sequence analysis that the clone comprised an appropriate sequence by determination of the oligonucleotide sequence inserted into pAdHM15-RGD.

Then, pHMCMVLacZ-1 was prepared by inserting β-galactosidase (LacZ) gene derived from pCMV β (Clontech) into a shuttle plasmid pHMCMV5 (H. Mizuguchi, M. A. Kay., A simple method for constructing E1 and E1/E4 deleted recombinant adenovirus vector. Hum. Gene Ther. 10 (1999) 2013–2017).

Subsequently, pAdHM15-RGD and pHMCMVLacZ-1, digested with I-CeuI/PI-SceI, were subjected to in vitro ligation to construct pAdHM15-RGD-LacZ (FIG. 2). The I-CeuI and PI-SceI, herein, are rare restriction enzymes recognizing a sequence consisting of at least 9 to 10 and 11 bases, respectively.

A plasmid pAdHM4 was ligated with another plasmid pHMCMVLacZ-1 to construct pAdHM4-LacZ, as a plasmid used for preparation of a control virus having a wild fiber protein.

Both of the above pAdEM15-RGD-LacZ and pAdHM4-LacZ comprised a Cytomegalovirus (CMV) promoter driving LacZ gene and a bovine growth hormone (BGH) polyadenylation signal.

The above two plasmids, pAdHM15-RGD-LacZ and pAdHM4-LacZ were digested with PacI to be linearized, and then the plasmids were subjected to phenol-chloroform extraction and ethanol precipitation for purification. The linear pAdHM15-RGD-LacZ and pAdHM4-LacZ were transfected to 293 cells to prepare the viruses (AdHM15-RGD-LacZ and AdHM4-LacZ) derived from each plasmid, and the viruses were subjected to a $CsCl_2$ step gradient ultracentrifugation, then a $CsCl_2$ linear gradient ultracentrifugation for purification.

The titer of viral particle was determined by spectroscopically measuring viral DNA according to the method of Maizel et al. (Maizel, J. V. J., White, D. O. and Schar ff, M. D. (1968). The polypeptides of adenovirus. I. Evidence for multiple protein components in the virion and a comparison of types 2, 7A, and 12. Virology. 36, 115–125). As a result, the titer of AdHM15-RGD-LacZ was $5.28 \times 10^{11}$ particle titer/mL, and the titer of AdHM4-LacZ was $2.02 \times 10^{12}$ particle titer/mL.

Moreover, a vector plasmid (pAdHM15-RGD or pAdHM15-RGD-LacZ) or a LacZ-expressed recombinant adenoviral DNA (AdHM15-RGD-LacZ) having a RGD peptide in a fiber was subjected to DNA restriction analysis (i.e. an electrophoresis on 0.7% agarose gel, using HindIII/PacI, Csp45I/PacI, HindIII or Csp45I as a restriction enzyme). Each lane was defined as follows:

Lane 1: 1 kb DNA ladder marker

Lane 2: pAdHM15-RGD digested with HindIII/PacI

Lane 3: pAdHM15-RGD digested with Csp45I/PacI

Lane 4: pAdHM15-RGD-LacZ digested with HindIII/PacI

Lane 5: pAdHM15-RGD-LacZ digested with Csp45I/PacI

Lane 6: AdHM15-RGD-LacZ viral DNA digested with HindIII

Lane 7: AdHM15-RGD-LacZ viral DNA digested with Csp45I

Figure 3A:
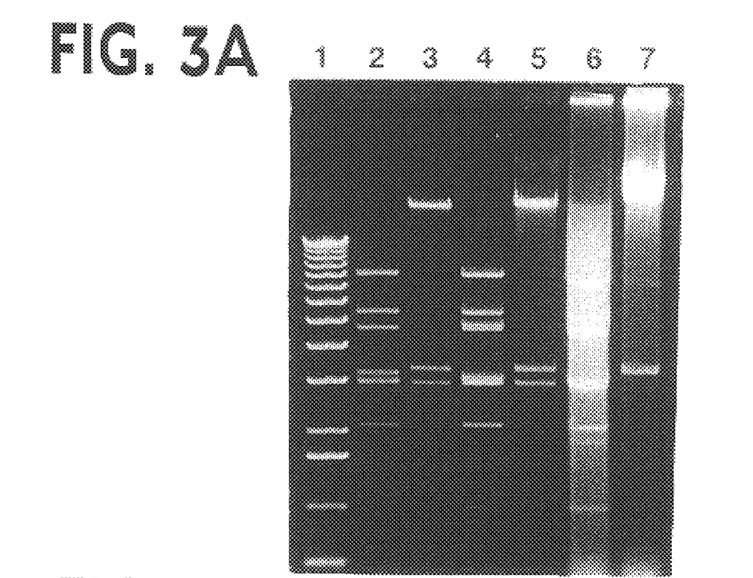
FIG. 3 shows the result of restriction endonuclease analysis. (A) Vector plasmid (pAdHM15-RGD or pAdHM15-RGD-LacZ) or LacZ expression recombinant adenovirus DNA having RGD peptide in the fiber (AdHM15-RGD-LacZ) are digested with HindIII/PacI, Csp45I/PacI, HindIII or Csp45I, followed by electrophoresis on 0.7% agarose gel.

The results are shown in FIG. 3A.

Results

Figure 3B:
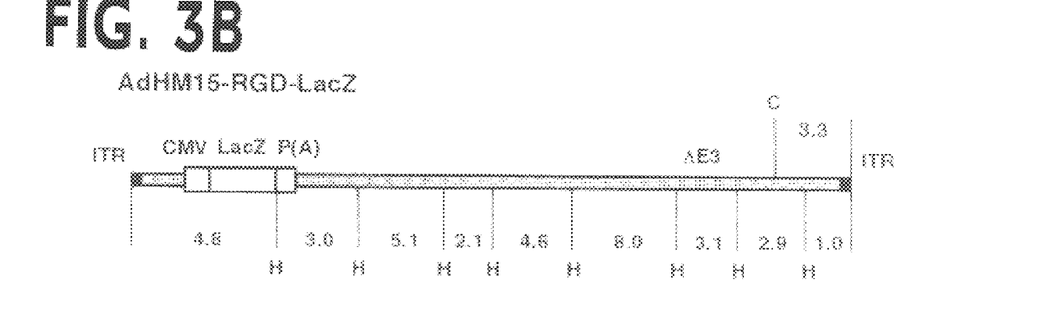

As a result of the above DNA restriction analysis, it was shown that a vector plasmnid which comprises or does not comprise a LacZ cassette, in other words, pAdHM15-RGD, pAdHM15-RGD-LacZ, or viral DNA AdHM15-RGD-LacZ comprised expected fragments as shown in Table 1. (FIG. 3).

TABLE 1

Length of fragment obtained by digesting pAdHM15-RGD, pAdHM15-RGD-LacZ and AdHM15-RGD-LacZ with each restriction enzyme

| Restriction enzyme | Length of fragment (kb) |
|---|---|
| pAdHM15-RGD | |
| HindIII/PacI | 3.0, 3.1, 5.1, 2.1, 4.6, 8.0, 3.1, 2.9, 1.0 |
| Csp45I/PacI | 3.0, 3.3, 26.6 |
| pAdHM15-RGD-LacZ | |
| HindIII/PacI | 3.0, 4.8, 3.0, 5.1, 2.1, 4.6, 8.0, 3.1, 2.9, 1.0 |
| Csp45I/PacI | 3.0, 3.3, 31.3 |
| AdHM15-RGD-LacZ | |
| HindIII | 4.8, 3.0, 5.1, 2.1, 4.6, 8.0, 3.1, 2.9, 1.0 |
| Csp45I | 3.3, 31.3 |

The gene transfer efficiency of the obtained vector AdHM15-RGD-LacZ was analyzed in Example 4 described later.

EXAMPLE 2

Preparation of Adenovirus Vector Having a Foreign Peptide Added to the HI Loop of the Fiber-2

The method for constructing a vector plasmid pAdHM15-RGD is as shown in Example 1.

pCMVL1 was prepared by inserting a luciferase (Luc) gene derived from pGL3-Control (Promega) into a shuttle plasmid pHMCMV6 (H. Mizuguchi, M. A. Kay., A simple method for constructing E1 and E1/E4 deleted recombinant adnovirus vector. Hum. Gene Ther. 10 (1999) 2013–2017).

Figure 4:
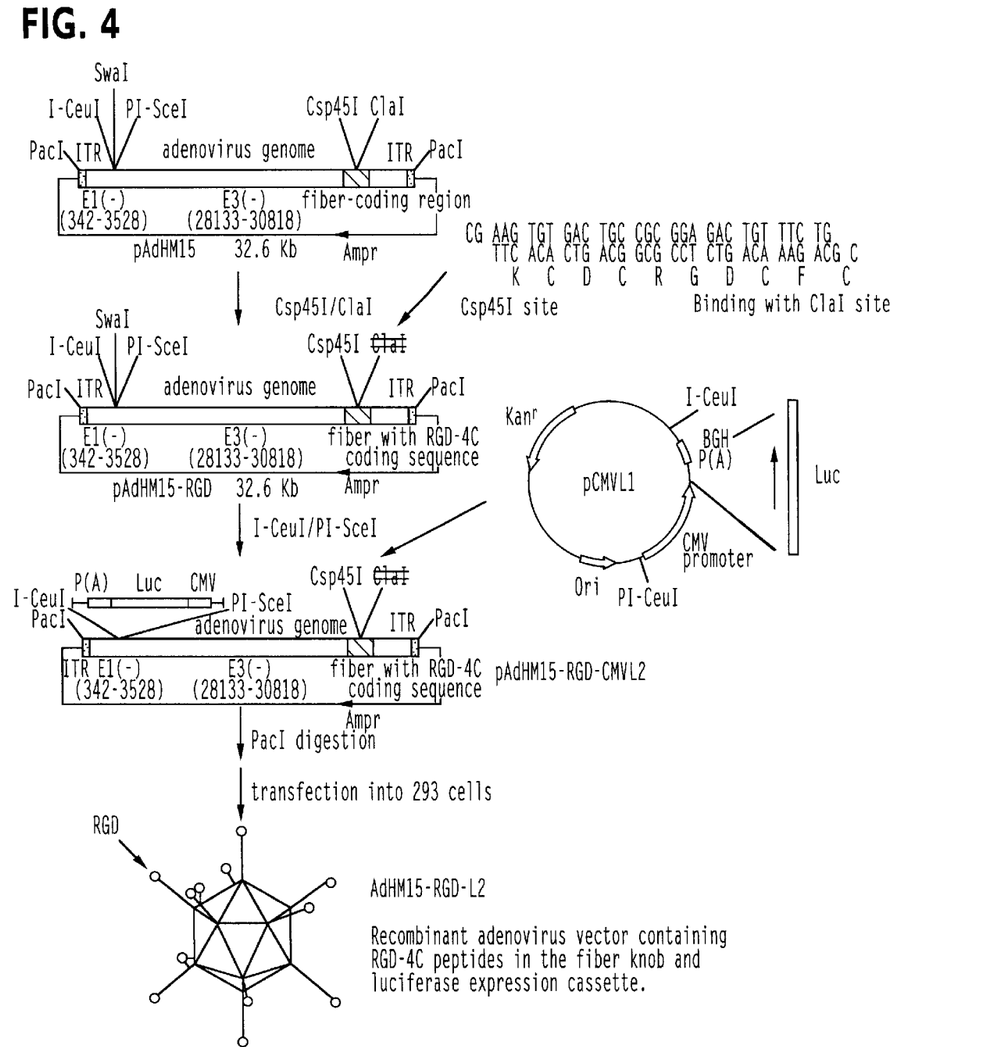
FIG. 4 (SEQ ID NOS 10, 11 & 14) is a plan for construction of an adenovirus vector containing RGD-4C peptide in the HI loop of the fiber knob, and containing a luciferase (Luc) expression cassette in E1-deletion region.

The above pAdHM15-RGD and pCMVL1 encoding luciferase were digested with I-CeuI/PI-SceI, and then these were ligated by in vitro ligation to construct pAdHM15-RGD-CMVL2 (FIG. 4).

pAdHM4-CMVL2 was constructed by ligating pAdHM4 and pCMVL1 which were plasmids for the preparation of a control virus having a wild fiber protein.

Both of the above pAdHM15-RGD-CMVL2 and pAdHM4-CMVL2 comprised a CMV promoter driving Luc gene and a BGH polyadenylation signal.

After that, the above two plasmids, pAdHM15-RGD-CMVL2 and pAdHM4-CMVL2 were digested with PacI to allow linearization, and then purified by phenol-chloroform extraction and precipitation with ethanol. The linearized pAdHM15-RGD-CMVL2 and pAdHM4-CMVL2 were transfected to 293 cells to prepare viruses (AdHM15-RGD-L2, AdHM4-L2) derived from each plasmid, and the viruses were then subjected to $CsCl_2$ step gradient ultracentrifugation, then $CsCl_2$ linear gradient ultracentrifugation for purification.

The gene transfer efficiency of the obtained vectors AdHM15-RGD-L2 and AdHM4-L2 (control) was analyzed in Example 5 described later.

EXAMPLE 3

Preparation of Adenovirus Vector Having a Foreign Peptide Added to the HI Loop of the Fiber-3

A method for constructing a vector plasmid pAdHM15 is as shown in Example 1.

NGR-associated peptide (CNGRCVSGCAGRC: SEQ ID NO: 6) was selected as a foreign peptide, and oligonucleotide DNAs (oligonucleotides 6 and 7) corresponding to this peptide were used.

First, pAdHM15 constructed as above was cleaved with Csp45I/ClaI, and then ligated with oligonucleotide 6 (5'-CGGCTGCAACGGCCGCTGCGTGAGCGGCTGC GCCGGCCGCTG-3', SEQ ID NO: 12) and oligonucleotide 7 (5'-CGCAGCGGCCGGCGCAGCCGCTCACGCAGCG GCCGTTGCAGC-3', SEQ ID NO: 13). Then, the above ligated DNA was introduced into an *Escherichia coli* DH5 strain to transform the strain, thereby obtaining pAdHM15-NGR.

The above pAdHM15-NGR and pCMVL1 were digested with I-CeuI/PI-SceI, and were ligated by in vitro ligation to construct pAdHM15-NGR-CMVL2. The above pAdHM15-NGR-CMVL2 comprised a CMV promoter driving Luc gene and a BGH polyadenylation signal.

After that, the above plasmid pAdHM15-NGR-CMVL2 was digested with PacI to allow linearization, and then purified by phenol-chloroform extraction and precipitation with ethanol. The linearized pAdHM15-NGR-CMVL2 was transfected to 293 cells to prepare a virus (AdHM15-NGR-L2) derived from the plasmid, and the virus was then subjected to $CsCl_2$ step gradient ultracentrifugation, then $CsCl_2$ linear gradient ultracentrifugation for purification.

The gene transfer efficiency of the obtained vector AdHM15-NGR-L2 was analyzed in Example 5 described later.

EXAMPLE 4

Analysis of Gene Transfer Efficiency-1

To examine the function of RGD-4C peptide which was inserted into a vector AdHM15-RGD-LacZ prepared in Example 1, the gene transfer efficiency of AdHM15-RGD-LacZ and AdHM4-LacZ (a control) were analyzed, using both SK-HEP1 cells which express CAR and are sensitive to adenovirus, and CHO cells insensitive to the virus (due to unexpressed CAR). SK-HEP1 cells are herein cells which were derived from human liver vascular endothelial cells, furnished by Dr. Mark A. Kay (Stanford Univ.). CHO cells herein were furnished by Tadanori Mayumi (Osaka Univ.)

First, SK-HEP1 and CHO cells were transformed with AdHM15-RGD-LacZ or AdHM4-LacZ (for both vectors, 1200, 8000 vector particles(VP)/cell were used) for 1.5 hours.

After 2 days, the expression of LacZ protein (i.e. LacZ enzyme activity) was confirmed by both luminescent assay with a Luminescent β-galactosidase detection kit (Clontech), and X-gal (5-bromo-4-chloro-3-indolyl-β-D-galactopyranoside) staining (FIG. 5). The level of LacZ enzyme activity was evaluated, using a standard substance attached to the kit as an indicator.

Results

Figure 5A:
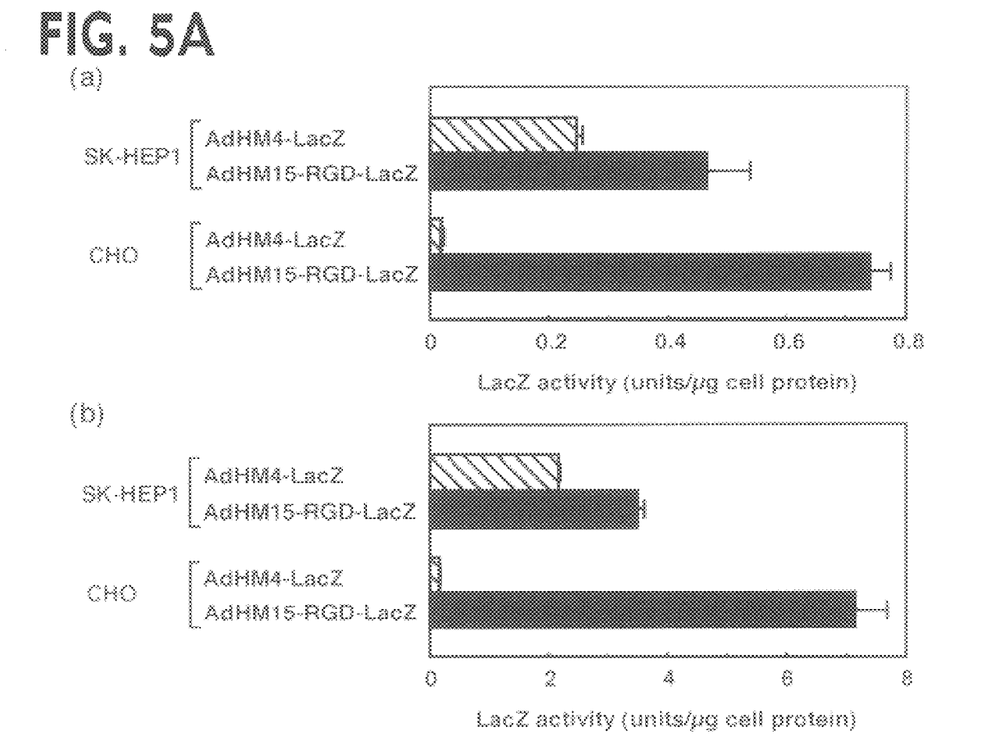
FIG. 5 shows comparison of LacZ expression among culture cells transduced with AdHM4-LacZ and those transduced with AdHM15-RGD-LacZ. (A) Results of measurement of LacZ expression with chemiluminescence assay. In (A), (a) and (b) show the results obtained by the use of the 1200 vector particles/cell and the 8000 vector particles/cell, respectively. Data are shown with average ±S.D. of data from 3 rounds of the test. (B) Results of X-gal staining for CHO cell (1200 vector particles/cell). In (B), (a) is the result for AdHM4-LacZ, and (b) AdHM15-RGD-LacZ.
Figure 5B:
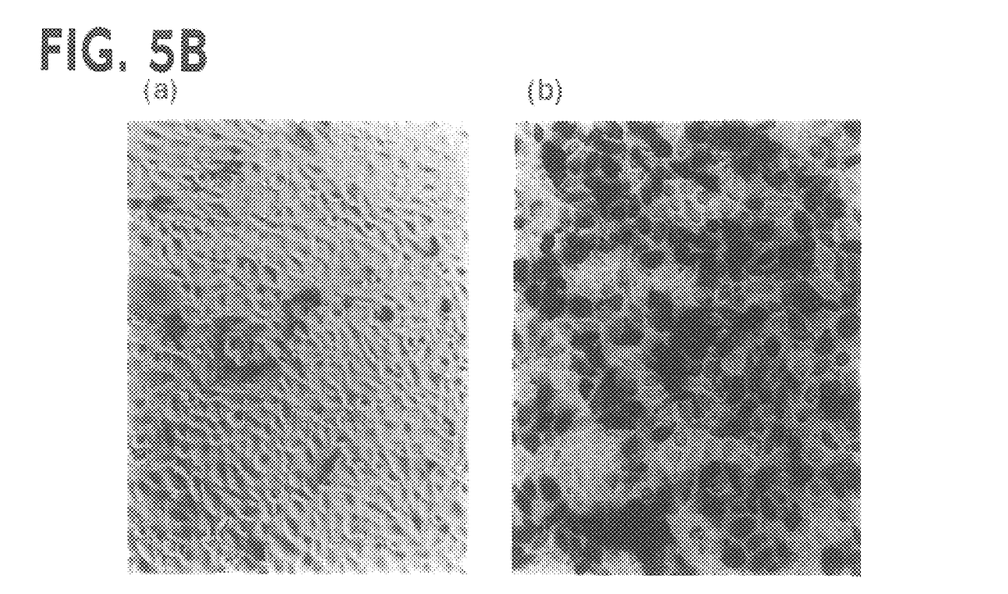

In SK-HEP 1 cells, LacZ enzyme activity detected after transformation by AdHM15-RGD-LacZ (a RGD fiber) and activity detected after transformation by AdHM4-LacZ (a wild fiber) differed by a factor of about 2 (FIG. 5A). In CHO cells, however, the difference reached a factor of 40, and activity was higher for transformation by AdHM15-RGD-LacZ. Furthermore, the ratio of X-gal positive cells in CHO cells which were transformed by AdHM15-RGD-LacZ and AdHM4-LacZ corresponded extremely well to the results of the above luminescent assay (FIG. 5B).

From these results, it was confirmed that AdHM15-RGD-LacZ having a RGD fiber can be transfected via an RGD-integrin bond as well as via an RGD-CAR bond, effectively introducing a gene (It is known that a penton-base RGD motif-integrin bond does not function as the $1^{st}$ step of transfection).

It is considered that, in SK-HEP1 cells, gene transfer efficiency by AdHM15-RGD-LacZ was somewhat higher than that by AdHM4-LacZ, because AdHM15-RGD-LacZ can be transfected both via CAR and via integrin.

Therefore, it was shown that the addition of RGD4C peptide to a fiber results in an effective gene transfer to CAR-deleted cells such as CHO cells.

EXAMPLE 5

Analysis of Gene Transfer Efficiency-2

To examine the functions of RGD-4C peptide inserted into a vector AdHM15-RGD-L2 prepared in Example 2 and NGR-associated peptide inserted into a vector AdHM15-NGR-L2 prepared in Example 3, the gene transfer efficiency of AdHM15-RGD-L2, AdHM15-NGR-L2 and AdHM4-L2 (a control) were analyzed, using both SK-HEP1 cells which have expressed CAR and are sensitive to adenovirus, and LN444 cells insensitive to the virus (due to unexpressed CAR). LN444 cells are herein human glioma cells which were furnished by Dr. Mitsuhiro Tada (Hokkaido Univ.), and the cells expressed RGD peptide target integrin (α v β 3 or α v β 5) and aminopeptidase N/CD13 on their cell surface.

First, SK-HEP1 and LN444 cells ($5 \times 10^4$ cells, respectively) were transformed with AdHM4-L2, AdHM15-RGD-L2, or AdHM15-NGR-L2 (100, 300, 1000, 3000 vector particles (VP) per cell, respectively) for 1.5 hours.

After 2 days, the expression of luciferase (Luc) protein (i.e. Luc enzyme activity) was confirmed by a luciferase reporter assay kit (Clontech) (FIG. 6).

Results

Figure 6A:
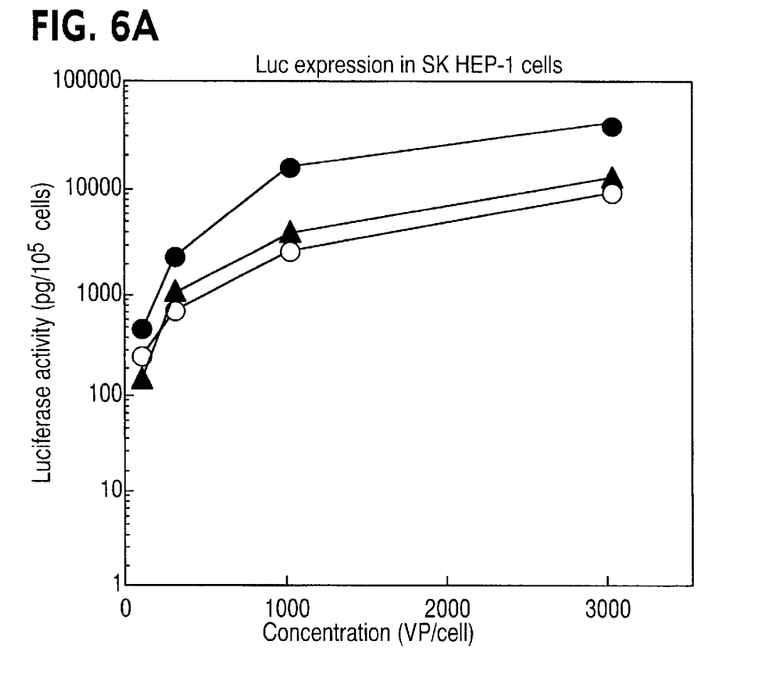
FIG. 6 shows comparison of Luc expression among culture cells transduced with AdHM4-L2, AdHM15-RGD-L2, or AdHM15-NGR-L2. AdHM4-L2 is shown with "○," AdHM15-RGD-L2 with "●," and AdHM15-NGR-L2 with "▲." (A) Results of measurement of Luc expression in SK HEP-1 cells. (B) Results of measurement of Luc expression in LN444 cells. Data are shown with average ±S.D. of data from 4 rounds of the test.

In SK-HEP 1 cells, Luc enzyme activity detected after transformation by AdHM15-NGR-L2 (an NGR fiber; ▲) and activity detected after transformation by AdHM4-L2 (a wild fiber as a control; ○) differed by a factor of about 2. However, when compared with a case of transformation by AdHM15-RGD-L2 (a RGD fiber; ●), the difference reached a factor of 10, and activity was higher for transformation by AdHM15-RGD-L2 (FIG. 6A).

Figure 6B:
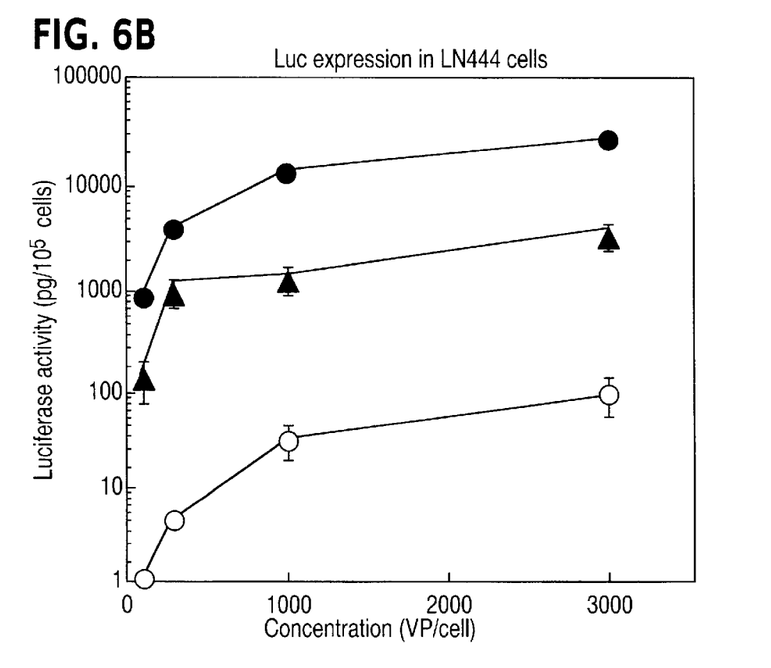

In LN444 cells, the difference between Luc enzyme activity detected after transfornation by AdHM15-NGR-L2 (▲) and activity detected after transformation by AdHM4-L2 (a control; ○) reached a factor of 100, and activity was higher for transformation by AdHM15-NGR-L2. Further, when compared with a case of transformation by AdHM15-RGD-L2 (●), the difference reached a factor of about 1,000 (FIG. 6B). The term "VP" in the horizontal axis of Example 6 is used to mean vector particles (the number of vector particles).

From these results, it was reconfirmed that AdHM15-RGD-L2 having a RGD fiber can be transfected via an RGD-integrin bond as well as via an RGD-CAR bond, effectively introducing a gene. Furthermore, it was also comfirmed that AdHM15-NGR-L2 having an NGR fiber can be transfected via an NGR-CD13 bond as well as via an RGD-CAR bond, effectively introducing a gene.

therefor, it was shown that the addition of NGR-associated peptide to a fiber results in an effective gene transfer to CD13 expression cells such as LN444 cells.

All publications cited herein are incorporated herein by reference in their entirety.

According to the method of the present invention, any peptide can be introduced into a fiber HI loop-coding gene sequence in one step of in vitro ligation. Therefor, an adenovirus vector having high gene transfer efficiency can be produced by simple operations.

What is claimed is:

1. A method for constructing a fiber-mutant adenovirus vector which comprises the following steps:
   (a) preparing a plasmid having a complete adenovirus genome except for the E1 and E3 regions,
   (b) inserting a Csp45I and/or ClaI recognition sequence into a fiber HI loop-coding gene sequence of the plasmid,
   (c) synthesizing an oligonucleotide having a foreign peptide-coding DNA and a Csp45I and/or ClaI recognition sequence, and
   (d) introducing the synthesized oligonucleotide directly into the fiber HI loop-coding gene sequence of the plasmid digested with the Csp45I and/or ClaI.

2. The method according to claim 1 wherein the foreign peptide is a peptide having tropism for tumor vascular endothelial cells.

3. The method according to claim 2 wherein the foreign peptide having tropism for tumor vascular endothelial cells is a peptide containing a tripeptide: R-G-D.

4. The method according to claim 2 wherein the peptide having tropism for tumor vascular endothelial cells is a peptide containing a tripeptide: N-G-R.

5. A fiber-mutant adenovirus vector which is constructed by the method according to claim 1.

6. A fiber-mutant adenovirus vector which is constructed by the method according to claim 2.

7. A fiber-mutant adenovirus vector which is constructed by the method according to claim 3.

8. A fiber-mutant adenovirus vector which is constructed by the method according to claim 4.

9. An adenovirus vector which comprises a Csp45I and/or ClaI recognition sequence in the fiber HI loop-coding gene sequence.

* * * * *